United States Patent [19]
Toepfer et al.

[11] Patent Number: 5,817,742
[45] Date of Patent: Oct. 6, 1998

[54] POLYMER-CONJUGATED MALONIC ACID DERIVATIVES AND THEIR USE AS MEDICAMENTS AND DIAGNOSTIC AGENTS

[75] Inventors: Alexander Toepfer, Kriftel; Gerhard Kretzschmar, Eschborn; Eckart Bartnik, Wiesbaden; Wolfgang Schmidt, Frankfurt; Brigitte Hörsch, Kriftel, all of Germany

[73] Assignee: Hoechst Aktiengesellschaft, Frankfurt, Germany

[21] Appl. No.: 718,524

[22] PCT Filed: Mar. 7, 1995

[86] PCT No.: PCT/EP95/00844

§ 371 Date: Sep. 11, 1996

§ 102(e) Date: Sep. 11, 1996

[87] PCT Pub. No.: WO95/24437

PCT Pub. Date: Sep. 14, 1995

[30] Foreign Application Priority Data

Mar. 11, 1994 [DE] Germany ............... 44 08 248.7

[51] Int. Cl.$^6$ .................................................. C08G 69/10
[52] U.S. Cl. ................ 528/328; 528/329.1; 528/330; 528/331; 528/332; 528/335; 528/363
[58] Field of Search ................. 528/328, 363, 528/329.1, 330, 331, 332, 335

[56] References Cited

U.S. PATENT DOCUMENTS 5,254,676  10/1993  Sabesan ........................... 536/4.1

FOREIGN PATENT DOCUMENTS

| 0 406 473 | 1/1991 | European Pat. Off. . |
|---|---|---|
| 273 443 | 11/1989 | Germany . |
| 91/19501 | 12/1991 | WIPO . |
| 91/19502 | 12/1991 | WIPO . |
| 92/00245 | 1/1992 | WIPO . |
| 92/09870 | 6/1992 | WIPO . |
| 92/18610 | 10/1992 | WIPO . |
| 92/22565 | 12/1992 | WIPO . |
| 93/14127 | 7/1993 | WIPO . |

OTHER PUBLICATIONS

Patent Abstract of Japan vol. 13, No. 372, (C–627) [3720] Aug. 1989 & JP,A,01 127039 (Chuichi Hirayama).

Yamazaki et al., "Studies Carbohydrate–Bind. Prot. Use Liposome–Based Sys.–1. Prep. of Neoglycoprotein–Conjug. Liposomes & Feasibil. Use as Drug–Targeting Devices", J. Biochem. vol. 24 No. 1, (1992) pp. 99–104.

Nishimura et al., "Synthetic Glycoconjugates 2.[1] n–Pentenyl Glyocosides as Convenient Mediators Syntheses of New Types of Glycoprotein Models", Macromolecules, vol.24, (1991) pp. 4236–4241.

Spaltenstein et al., "Polyacrylamides Bearing Pendant a:Sialoside Groups Strongly Inhibit Agglutination of Erythrocytes by Influenza Virus", J. Am. Chem. Soc. vol. 113, (1991) pp. 686–687.

Connolly et al., "Binding and Endocytosis of Cluster Glycosides by Rabbit Hepatocytes", Journal of Biological Chemistry, vol. 25, No. 2, (1982) pp. 939–945.

Rathi et al., "N–(2–Hydroxypropyl)methacrylamide Copolymers Containing Pendant Saccharide Moieties . . . ", Journal of Polymer Science Part A: Polymer Chemistry, vol. 29, (1991), 1895–1902.

DeFrees et al., "Ligand Recognition by E–Selectin: Analysis of Conformation and Activity of Synthetic Monomeric and Bivalent Sialyl Lewis X Analogs", J. Am. Chem. Soc. vol. 115, (1993) p. 7549–7550.

Houghton et al., "Monoclonal Antibodies: Potential Applications to the Treatment of Cancer", Seminars in Oncology, vol. 13, No. 2, (1986) pp. 165–179.

Ravindranath et al., "An Epitope Common to Gangliosides O–Acetyl–G$^{D3}$ and G$^{D3}$ Recognized by Antibodies in Melanoma Patients After Active Specific Immunotherapy[1]", Cancer Res. vol. 49, (1989) pp. 3891–3897.

Eckelman et al., "In Vivo Diagnosis and Therapy of Human Tumors with Monoclonal Antibodies", Proceedings of a Symposium held in Naples, Italy, (1988) pp. 100–185.

Chem Abstract, vol. 1 ed: 56557, Sep. 4, 1997.

*Primary Examiner*—Duc Truong
*Attorney, Agent, or Firm*—Foley & Lardner

[57] ABSTRACT

Polymer-based polyvalent malonic acid derivatives having anti-adhesive properties are described. The compounds comprise a polyamino acid linked to a group of formula (I). In formula (I), $R^1$ and $R^2$ together form a six-membered carbocylic or heterocyclic ring, containing at least one substituent selected from $R^4$, $R^5$, and $R^6$. $R^3$ is H, $(CH_2)_mX$ or $CH_2O(CH_2)^mX^1$. The polyamino acid and the group of formula II are linked via $R^4$, $R^5$, or $R^6$, or optionally via a spacer of formula $-[Q^1-(CH_2)_p-Q^2-]_r$. A and B independently are O, S, NH, HN—CO, OC—NH, O—CO, OC—O, NH—CO—O, —O—CO—NH, S—CO, SC—O, O—CS—S, S—CS—OS, NH—CS—S, S—CS—NH, or $CH_2$. Z is a pyranose, furanose, open-chain polyalcohol or Y—$X^6$. Y is —O—$(CX^2,X^3)_n$, -$(CX^2,X^3)_n$, —$CH_2$—$(CX^2,X^3)_n$ or a saturated or unsaturated six-membered carbo- or heterocyclic group having at least one substituent $R^9$, or a combination of the chain —O—$(CX^2,X^3)_n$, or -$(CX^2,X^3)_n$, and the carbocyclic or heterocyclic group, in which $R^4$, $R^5$, and $R^6$ independently are H, OH, —O—$(CH_2)_qX^4$, —$CH_2O(CH_2)_qX^5$, or $HNC(O)CH_3$, and X, $X^1$, $X^2$, and $X^3$ independently are H, $NH_2$, COOH, OH, $CH_2OH$, $CH_2NH_2$, $C_1$–$C_{20}$-alkyl, or $C_6$–$C_{10}$-aryl, $X^4$ and $X^5$ independently are —NH— or —O—, and $X^6$ is OH or —$C(R^3)$ $(COOH)_2$. m, n, and q independently can be 1–20. In the linker, $Q^1$ is $CH_2$ or —CO—, $Q^2$ is —NH— or —CO—NH—, p is 1–6, and r is 0 or 1. Methods of preparing the compounds, and their use as medicaments or diagnostic agents also are disclosed.

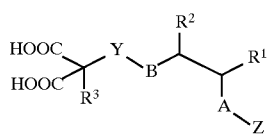

20 Claims, No Drawings

POLYMER-CONJUGATED MALONIC ACID DERIVATIVES AND THEIR USE AS MEDICAMENTS AND DIAGNOSTIC AGENTS

The present invention relates to polyvalent polymer-based malonic acid derivatives having antiadhesive properties which cause intolerance reactions in vivo neither in their entirety nor in the form of degradation products, and to their preparation process and their use as medicaments and diagnostics.

The glycoconjugates present on the surface of eukaryotic cells represent specific bonding isotopes for transmembrane proteins which are called selectins. These selecting, which occur both in the endothelium and on the various circulating cells of the hematolymphatic system, undergo specific interactions with carbohydrate epitopes (ligands) of the other respective cell type (K. A. Karisson, TIPS 12, (1991), 265–272).

Synthetic analogs of selectin ligands are therefore promising candidates for anti-inflammatories and anticoagulants. Carbohydrate ligands also play a decisive role as recognition domains for viruses, bacteria and toxins, and therefore also in the initiation of the corresponding diseases (prophylaxis, diagnosis or treatment of bacterial and viral infections, inflammatory diseases, rheumatic arthritis, allergies, post-infarction syndrome, shock, apoplexy, acute and chronic organ rejection, vasculitis, sepsis, shock lung and the like).

Since cancer cells have a different pattern of these carbohydrate structures from healthy cells, this enables these mimetics to be used on the one hand as labels, and on the other hand for combating tumor cells, especially in metastasing tumors (S. I. Hakomori, Cancer Cells, December 1991, Volume 3, No. 12).

Sialylated and/or fucosylated carbohydrates, such as, for example, sialyl-Lewis X and sialyl-Lewis A, are of particular importance as mediators for cell adhesion (Lowe et al., Cell, 63, 475–85, 1990).

Simpler structures have already been proposed and in some cases synthesized with the aim of simplifying the very involved syntheses of these compounds while retaining or improving their bonding affinity to the corresponding selecting. Thus, for example, neuraminic acid has been replaced by lactic or glycolic acid and/or fucose has been replaced by glycerol or trifluoromethylfucose and/or N-acetylglucosamine has been replaced by glucosamine or glucose (PCT/US 92/09870). Substitution of neuraminic acid by sulfate or phosphate has also been described (PCT/CA 92/00245). Substitution of glucosamine by a chain of at least 2 carbon atoms is also described (WO 92/18610).

Treatment of inflammatory diseases with free oligosaccharides, which are said to bond to receptors instead of the naturally occurring ligands, is unsuccessful because of the very high amounts of oligosaccharide to be administered, since the affinity between the receptor and oligosaccharide is low ($K_D \sim 10^{-4}$M for the interaction between a monovalent galactoside and the corresponding lectin, D. T. Connolly et al. J. Biol. Chem. 257, 939, (1982)).

Divalent structures having a better bonding, in some cases, to the particular receptor are described by Wong et al. (J. Am. Chem. Soc. 115, 7549 (1993)) and in U.S. Pat. No. 5,254,676.

It is also known that an increased interaction between the receptor and ligand is achieved by coupling several ligands to a surface. Using the example of the virus protein hemagglutinin, which bonds to neuraminic acid on the cell surface, it has been possible to demonstrate how the use of a polymer having this polyvalent effect has a significant effect on the ligand-receptor interaction (monovalent $K_D=2\times 20^{-4}$M, polyvalent $K_D=3\times 10^{-7}$M, A. Spaltenstein et al. J. Am. Chem. Soc. 113, 686 (1991)). Surfaces which have been used to date are liposomes (N. Yamazaki, Int. J. Biochem. 24, 99 (1991); WO 91/19501; WO 91/19502), polyacrylamides (R. C. Rathi et al. J. Polym. Sci.: Part A: Polym. Chem. 29, 1895 (1991), S. I. Nishimura et al. Macromolecules 24, 4236 (1991)), polylysine or sulfated polysaccharides. These polyvalent structures have the disadvantage of either having only a low stability in vivo or not being tolerated in vivo owing to their breakdown into toxic metabolites. In the case of polylysine or sulfated polysaccharides, nonspecific interactions with cell surface structures occur.

The object of the present invention is to provide polyvalent polymer-based malonic acid derivatives having antiadhesive properties which cause intolerance reactions in vivo neither in their entirety nor in the form of degradation products. These should have a comparable or more potent interaction with the receptor, compared with the naturally occurring ligands, and should be easier to prepare in larger amounts, compared with the naturally occurring carbohydrate ligands.

It is furthermore an object of the present invention to provide, on the basis of these polymeric and polyvalent malonic acid derivatives, medicaments for treatment or prophylaxis and compositions for diagnosis of diseases which involve bacterial or viral infections, metastasing tumors or inflammatory processes.

This object is achieved according to the invention by a compound consisting of a polyamino acid which is linked in each case by a spacer of the formula I

in which
  $Q^1$ is —$CH_2$— or

$Q^2$ is —NH— or

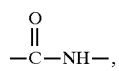

p is a number from 1 to 6 and
  r is 0 or 1,
with at least one radical of the formula II

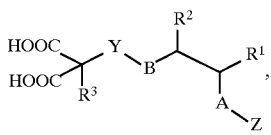

in which
  $R^1$ and $R^2$ together form a six-membered carbo- or heterocyclic radical having at least one of the ring substituents $R^4$, $R^5$ and $R^6$ and
  $R^3$ is H, $(CH_2)_m X$ or $CH_2O(CH_2)_m X^1$,
  A and B independently of one another are O, S, NH, HN—CO, OC—NH, O—CO, OC—O, NH—CO—O, O—CO—NH, S—CO, SC—O, O—CS—S, S—CS—O, NH—CS—S, S—CS—NH or $CH_2$ and
  Z is a pyranose, a furanose, an open-chain polyalcohol or Y—$X^6$, Y is —O—(CX$^2$,X$^3$)$_n$, —(CX$^2$,X$^3$)$_n$, —CH$_2$—(CX$^2$,X$^3$)$_n$ or a saturated or unsaturated six-membered carbo- or heterocyclic radical having at least one substituent R$^9$, or a combination of the chain —O—(CX$^2$,X$^3$)$_n$ or —(CX$^2$,X$^3$)$_n$ and the carbo- or heterocyclic radical, in which R$^4$, R$^5$ and R$^6$ independently of one another are H, OH, —O—(CH$_2$)$_q$X$^4$, CH$_2$O(CH$_2$)$_q$X$^5$ or HNC(O)CH$_3$ and X, X$^1$, X$^2$ and X$^3$ independently of one another are H, NH$_2$, COOH, OH, CH$_2$OH, CH$_2$NH$_2$, C$_1$–C$_{20}$-alkyl or C$_6$–C$_{10}$-aryl, X$^4$ and X$^5$ independently of one another are —NH— or —O— and X$^6$ is OH or

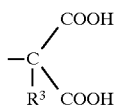

and m, n and q independently of one another are a number from 1 to 20, via one of the ring substituents R$^4$, R$^5$ or R$^6$.

The polyamino acid is preferably polysuccinimide, polyaspartamide, polyglutamate or polylysinefumaramide, or the polyamino acid is a copolymer of polysuccinimide and polyaspartamide, a copolymer of polyhydroxyethylaspartamide and polyaspartamide or a copolymer of polysuccinimide, polyaspartamide and polyhydroxyethylaspartamide.

The compound according to the invention is preferably distinguished by the fact that in the radical of the formula II, R$^1$ and R$^2$ together form a substituted tetrahydropyran ring, A and B are O, z is a -fucopyranosyl group and Y is (CX$^2$,X$^3$)$_n$, in which R$^3$, X$^2$ and X$^3$ are H and n is 5.

Preferably, the substituents of the tetrahydropyran ring R$^4$ and R$^5$ are each H, the substituent R$^6$ in the tetrahydropyran ring between the ring hetero atom O and the ring substituent —A—Z is —CH$_2$O(CH$_2$)$_q$X$^5$ and X$^5$ is —NH—; q is particularly preferably 2.

The tetrahydropyran ring is preferably a pyranose.

The pyranose is particularly preferably N-acetyl-D-glucosamine.

Preferably, in the compound according to the present invention, R$^1$ and R$^2$ together are a six-membered carbocyclic radical, A—Z is

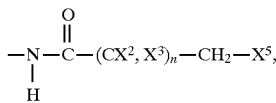

—B—Y— is

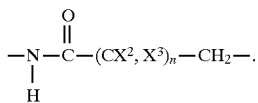

R$^3$ and X$^2$ are H, X$^3$ and X$^6$ are OH and n is 4, or, alternatively,

X$^6$ is

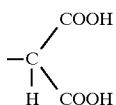

The abovementioned object is furthermore achieved by a process for the preparation of the compound described above, which comprises achieving the covalent linkage of the polymer with a compound of the formula III

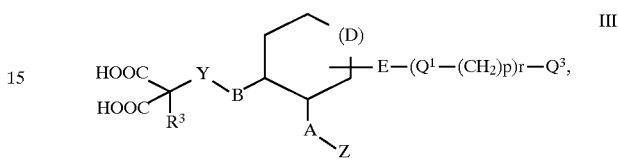

in which (D) is —NH—, —O— or —CH$_2$—,

E if r=1 is —O—(CH$_2$)$_q$—NH—, —O—(CH$_2$)$_q$—O—, —CH$_2$O(CH$_2$)$_q$—NH— or —CH$_2$O(CH$_2$)$_q$—O— and if r=0 is —O—(CH$_2$)$_q$—, —O—(CH$_2$)$_q$—, —CH$_2$O(CH$_2$)$_q$— or —CH$_2$O(CH$_2$)$_q$—O— and Q$^3$ is —OH, —NH$_2$ or

and the other variables have the abovementioned meanings, by reaction between a reactive and an activated group.

The object is furthermore achieved by a medicament comprising the compound according to the present invention and, if appropriate, pharmaceutical carriers.

The compound according to the present invention is advantageously suitable for the preparation of a medicament for treatment or prophylaxis of diseases in which bacterial or viral infections, inflammatory processes or metastasing tumors are involved.

The compound according to the invention is advantageously also suitable for the preparation of a composition for diagnosis of diseases in which bacterial or viral infections, inflammatory processes or metastasing tumors are involved.

The invention is described in detail below, in particular in its preferred embodiments:

The polyvalent polymer-based malonic acid derivative is physiologically tolerated and preferably has a molecular weight of <70 kD. Tolerated well means that no intolerance reactions are caused by the compound. The malonic acid derivative and the polymer by themselves should not be harmful to the organism in vivo, that is to say they should not have a hemolytic, antigenic or thrombogenic action. The polyvalent malonic acid derivative is physiologically degradable, i.e. it can be excreted in vivo as the whole molecule or can be degraded in vivo to small physiologically tolerated units, so that it can be excreted in this form (biodegradable). This particularly applies to the polymer. The residence time at the particular receptor and therefore the action time is controlled via the degradability in vivo. Thus, for example, the degradability can be controlled via the choice of polymer units and their linkage. Accumulation in the organism can thus be prevented in the event of an excess of the compound.

The terms receptor and ligand are defined as follows: A receptor is a macromolecule on the surface of the cell which, because of its configuration, has a bonding site for specific bonding of one, and in rare cases more, signal substances. This signal substance is called a ligand. The aim of bonding of the ligand to the receptor is transfer of information into the cell and subsequent modification of cell metabolism.

The degree of occupancy of the polymer with the malonic acid derivative indicates the percentage content of recurring units of the polymer onto which the malonic acid derivative is linked, based on the total number of recurring units.

In principle, synthesis is carried out by covalent linking of the malonic acid derivative to a polymer via a spacer.

The spacer is a physiologically tolerated, naturally occurring or synthetic compound which has the task of spatial separation of the malonic acid derivative and polymer. This spatial separation is necessary to ensure optimum accessibility of the ligand for the receptor. In order to ensure coupling of the spacer to the malonic acid derivative, the spacer must be bifunctional.

Biodegradable hydrophilic polymer is prepared by processes known to the expert. These are described, for example, in: H. G. Elias, Makromoleküle [Macromolecules], Volumes 1 and 2, Huthig and Wepf Verlag, Basle, Switzerland, 1991/92 or D. Braun, H. Cherdron, W. Kem, Praktikum der Makromolekularen Organischen Chemie [Practical Macromolecular Organic Chemistry], Hüthig Verlag 1979. Polymers which, in their function as carriers, are a constituent of the polyvalent malonic acid derivative and are to be used diagnostically or therapeutically must in principle meet a number of requirements in order to be tolerated well physiologically:

induce no immune response and avoid non-specific interactions and cumulation in the reticuloendothelial system.

According to the definition, the polymer consists of at least two identical or different monomer units which are linked with one another in linear or branched form and can have a molecular weight distribution.

The polymer is preferaoly a polyamino acid linked as a polyamide or polyanhydride and having a molecular weight of less than or equal to 70 kD. The polymer preferably has a minimum size of 2 kD in order to achieve an increased residence time in the blood compared with low molecular weight carriers.

Polyamino acids which are particularly suitable for preparation of polymer-based malonic acid derivatives are polyaspartamides, polysuccinimides, polyglutamates and polylysinefumaramides, as well as copolymers thereof.

The degree of occupancy of the polymer by the malonic acid derivative via a spacer is between 0.5 and 50 mol %, preferably between 2 and 25 mol %.

The polymer can be a carrier of several malonic acid derivatives coupled via spacers, or can carry only one malonic acid derivative. The number of malonic acid derivatives carried by the polymer depends on the medicinal use and the activity of the polyvalent malonic acid derivative according to the invention.

Covalent linking of the polymer with the spacer or with a compound comprising a covalently linked spacer and malonic acid derivative is achieved by reaction between a reactive and an activated group. It is possible here both for the reactive group to be at the end of the spacer or of a compound comprising a covalently linked spacer and malonic acid derivative and the activated group on the side of the polymer, and for the activated group to be on the end of the spacer or of a compound of a covalently linked spacer and malonic acid derivative and the reactive group on the side of the polymer.

A reactive group on the side of the malonic acid derivative or spacer can be an OH, $NH_2$ or COOH group. An activated group on the side of the polymer or spacer can be a carbamate, for example a nitrophenyl carbamate, a hydroxysuccinimide derivative, a carboxylic acid anhydride or an active ester accessible from the free carboxylic acid by known methods from peptide chemistry (for example succinimide ester, hydroxysuccinimide ester, mixed anhydride and the like).

The reaction between the reactive and activated groups is carried out by processes known to the expert for alkylation, acylation or addition onto a double bond. These processes are known to the expert from the literature (Larock, R.C. Comprehensive Organic Transformations, 1989, VCH Verlagsgesellschaft Weinheim).

If the activated group is an amino group and the reactive group is a carboxylic acid, the covalent linkage is achieved by the activation methods customary in peptide chemistry (carbodiimide, active ester, mixed anhydrides).

The polymer-conjugated malonic acid derivatives according to the invention can have a higher affinity for the natural receptors, for example for E- and P-selectin, than the naturally occurring carbohydrate ligands, as can be demonstrated with the aid of the cell adhesion assay described below.

1. 96-well microtiter test plates (Nunc Maxisorb®) are incubated at room temperature for 2 hours with 100 µl of a goat anti-human IgG antibody (Sigma®) diluted (1+100) in 50 mM Tris pH 9.5. After the antibody solution has been removed, the plates are washed once with PBS.

2. 150 µl of the blocking buffer are left in the wells at room temperature for 1 hour. The composition of the blocking buffer is: 0.1% of gelatin, 1% of BSA, 5% of calf serum, 0.2 mM PMSF, 0.02% of sodium azide. After removal of the blocking buffer, the plates are washed once with PBS.

3. In each case 100 µl of cell culture supernatant from correspondingly transfected and expressed COS cells are pipetted into the wells. Incubation is carried out at room temperature for 2 hours. After removal of the cell culture supernatant, the plates are washed once with PBS.

4. 20 µl of binding buffer are introduced into the wells. The binding buffer has the composition: 50 mM hepes, pH 7.5; 100 mM NaCl; 1 mg/ml of BSA; 2 mM $MgC_2$; 1 mM $CaCl_2$; 3 mM $MnCl_2$; 0.02% of sodium azide; 0.2 mM PMSF. 5 µl of the test substance are pipetted in and the components are mixed by swirling the plate and incubated at room temperature for 10 minutes.

5. 50 ml of a HL60 cell culture with 200,000 cells/ml are centrifuged at 350 g for 4 minutes. The pellet is resuspended in 10 ml of RPMI 1640 and the cells are centrifuged again. For labeling the cells, 50 µg of BCECF-AM (Molecular Probes®) are dissolved in 5 µl of anhydrous DMSO; 1.5 ml of RPMI 1640 are then added to the BCECF-AM/DMSO solution. The cells are resuspended in this solution and incubated at 37° C. for 30 minutes. After centrifugation at 350 g for two minutes, the marked cell pellet is resuspended in 11 ml of binding buffer and the resuspended cells are distributed in 100 µl aliquots into the microtiter plate wells. The plate is left to stand at room temperature for 10 minutes in order to allow the cells to sediment on the bottom of the test plate. The cells thus have the opportunity to adhere to the coated plastic.

6. To stop the test, the microtiter plate is immersed entirely, at an angle of 45°, into the stopping buffer (25 mM Tris, pH 7.5; 125 mM NaCl; 0.1% of BSA; 2 mM MgCl$_2$; 1 mM CaCl$_2$; 3 mM MnCl$_2$; 0.02% of sodium azide). The stopping buffer is removed from the wells by inverting and the procedure is repeated twice more.

7. The BCECF-AM-labeled cells firmly adhering in the wells are measured in a cytofluorimeter (Millipore®) at a sensitivity setting of 4, an excitation wavelength of 485/22 nm and an emission wavelength of 530/25 nm.

The polymer-conjugated malonic acid derivatives according to the present invention are all potential ligands for the selectins known to date (proteins which are expressed on the endothelium and other cell surfaces and bond to specific carbohydrate ligands).

The polymer-conjugated malonic acid derivatives according to the invention can accordingly be employed as anti-adhesion therapeutics and, in the case of inflammations, prevent the ELAM-1 receptors on stimulated endothelial cells bonding to sialyl-Lewis X structures on the surface of leukocytes. In the case of influenza treatment, the polymer-conjugated malonic acid derivatives prevent viruses from becoming attached to the neuraminic acid on the cell surface and therefore also prevent endocytosis of the virus particles.

These circumstances result in the possibility of prophylaxis, diagnosis or treatment of selectin-mediated diseases. These include, for example:

1. Autoimmune diseases: rheumatoid arthritis, multiple sclerosis, inflammatory bone diseases, lupus, myasthenia gravis, allergies, osteoarthritis, asthma, contact dermatitis, psoriasis, adult respiratory distress syndrome, transplant rejection.
2. Infections: colds, influenza, Helicobacter pylori, malaria, septic shock.
3. Cancer: colorectal, breast, ovarian, prostate.
4. Central nervous system: apoplexy, trauma
5. Reperfusion damage: myocardial infarction, angioplasty, unstable angina, systemic shock
6. Others: osteoporosis, wounds and severe burns.

The medicaments according to the invention are in general administered intravenously, orally or parenterally or as implants, but rectal use is also possible in principle. Suitable solid or liquid pharmaceutical formulation forms are, for example, granules, powders, tablets, coated tablets, (micro) capsules, suppositories, syrups, emulsions, suspensions, aerosols, drops or injectable solutions in ampule form and preparations having a protracted release of the active compound, for the preparation of which carriers and additives and/or auxiliaries are usually used, such as disintegrants, binders, coating agents, swelling agents, lubricants or glidants, flavorings, sweeteners or solubilizing agents. Frequently used carriers and auxiliaries which may be mentioned are, for example, magnesium carbonate, titanium dioxide, lactose, mannitol and other sugars, talc, milk protein, gelatin, starch, vitamins, cellulose and its derivatives, animal and vegetable oils, polyethylene glycols and solvents, such as, for example, sterile water, alcohols, glycerol and polyhydric alcohols.

The pharmaceutical preparations are preferably prepared and administered in dosage units. Solid dosage units are tablets, capsules and suppositories.

Different daily doses are needed for treatment of a patient, depending on the activity of the compound, the method of administration, the nature and severity of the disease and the age and body weight of the patient. Under certain circumstances, however, higher or lower daily doses may also be appropriate. The daily dose can be administered both by a single administration in the form of an individual dosage unit or of several small dosage units, and by several administrations of subdivided doses at certain intervals of time. The daily dose to be administered can furthermore depend on the number of receptors expressed during the course of the disease. It is conceivable that only a few receptors are expressed on the cell surface in the initial state of the disease, and accordingly the daily dose to be administered is lower than in the case of seriously ill patients.

The medicaments according to the invention are prepared by bringing a polymer-conjugated malonic acid derivative according to the present invention into the or a suitable administration form with customary carriers and, if appropriate, additives and/or auxiliaries.

The compound according to the present invention is also suitable for the preparation of antibodies for diagnostic determination of ligands which are not accessible, are not sufficiently immunogenic or are unknown.

In the case of many autoimmune diseases and tumors, certain ligands and antigens are highly regulated on the cell membrane. However, these are often unknown, cannot be isolated in the pure form or are not sufficiently immunogenic to be able to prepare antibodies therefrom.

The compound according to the present invention can be used for isolation of antibodies which undergo cross-reactions with epitopes of the naturally occurring unknown or inaccessible ligands. In addition to the diagnostic uses, therapeutic uses are also conceivable for the antibodies isolated in this manner (A. N. Houghton, D. A. Scheinberg, Semin. Oncol. 13 (1986) 165–179; W. C. Eckelmann, In Vivo Diagnosis and Therapy of Human Tumors with Monoclonal Antibodies; Pergamon Press, London 1988; M. H. Ravindranath, D. L. Morton, R. F. Irie, Cancer Res. 49 (1989) 3891–3897).

Specifications for the synthesis of a polymer-conjugated malonic acid derivative according to the invention are described by way of example below.

EXAMPLE 1

Synthesis of 4,6-isopropylidene-1,2-dideoxyglucose (1):

A solution of tri-O-acetyl-D-glucal (30 g, 110.17 mmol) in dioxane (400 ml) is hydrogenated with palladium-on-charcoal (10%, 3 g) in a hydrogen atmosphere for 24 hours. The mixture is filtered through kieselguhr and concentrated. To split off the acetyl groups, the residue is taken up in methanol (500 ml), and a 1M sodium methanolate solution (6 ml) is added. After 90 minutes, the mixture is neutralized with Amberlite IR-120 and filtered and the filtrate is concentrated in vacuo. The residue is coevaporated with toluene (3×250 ml) and taken up in DMF (500 ml). Dimethoxypropane (140 ml, 114.6 mmol) and p-toluenesulfonic acid (400 mg) are added to the solution. After 18 hours, triethylamine (3 ml) is added and the mixture is stirred for a further 15 minutes and concentrated under a high vacuum. Chromatography (toluene/acetone 4:1) gives 1d (33 g, 80%).

$^1$H NMR (300 MHz, CDCl$_3$): δ=1.41, 1.51 (2s, 6H, 2 CH$_3$), 1.76 (ddd, 1H, 2-H), 2.0 (ddd, 1H, 2-H), 2.8 (d, 1H, OH), 3.16 (m, 1H, 1-H), 3.46 (dd, 1H, 6-H), 3.53 (m, 1H, 1-H), 3.7 (dd, 1H, 6-H), 3.86 (dd, 1H, 4-H), 3.96 (m, 1H, 5-H).

Synthesis of 4-allyloxy-1-p-toluenesulfonyloxy-pentane (2):

A mixture of pentanediol (21.8 ml, 207 mmol), allyl bromide (11.7 ml, 138 mmol), potassium carbonate (21 g, 151.8 mmol) and dibenzo-18-crown-6 is treated in an ultrasonic bath for 24 hours. It is then diluted with methylene chloride (250 ml) and washed 2× with water (100 ml each time). The organic phase is dried over magnesium sulfate and concentrated and the residue is stirred with pyridine (50 ml, 600 mmol), methylene chloride (700 ml) and p-toluenesulfonyl chloride (40 g, 207 mmol). After 16 hours, the mixture is washed with saturated sodium chloride solution and the organic phase is dried and concentrated. Flash chromatography (hexane/ethyl acetate 6:1→5:1) gives compound 2 (19.9 g, 53%)

$^1$H NMR (300 MHz, CDCl$_3$): δ=1.39, 1.53, 1.66 (3m, 6H, —CH$_2$—CH$_2$—CH$_2$—), 2.45 (s, 3H, CH$_{3tos}$), 3.38 (t, 2H, OCH$_2$—), 3.93 (m, 2H, O—CH$_2$—CH=CH$_2$), 4.01 (t, 2H, OCH$_2$—), 5.20 (m, 2H; O—CH$_2$—CH=CH$_2$), 5.88 (m, 1H, O—CH$_2$—CH=CH$_2$), 7.34, 7.78 (2 m, 4H, tosyl-H$_{aromat}$).

Synthesis of 4-allyloxy-1-hydroxybutyl-(1→3)-1,2-dideoxyglucose (3):

Sodium hydride (1.56 g, 65 mmol) is added to a solution of 1 (10 g, 53.47 mmol) in dimethylformamide (100 ml). After 30 minutes, a solution of 2 (19 g, 63.8 mmol) is added dropwise. After 18 hours, water (5 ml) is added, the mixture is diluted with ether and the organic phase is washed with water and then concentrated. The residue is taken up in tetrahydrofuran (150 ml) and 1M hydrochloric acid (5 ml) and the mixture is heated at 60° C. After 90 minutes, it is concentrated in vacuo and the residue is coevaporated with toluene and chromatographed with hexane/ethyl acetate 1:1→1:3. 3 (12.1 g, 83%) is obtained.

$^1$H NMR (300 MHz, CDCl$_3$): δ=2.02 (m, 1H, 2-H), 2.58 (bt, 1H, OH), 3.93 (m, 2H, O—CH$_2$—CH=CH$_2$), 5.22 (m, 2H, O—CH$_2$—CH=CH$_2$), 5.92 (m, 1H, O—CH$_2$—CH=CH$_2$).

Synthesis of 4-allyloxy-1-hydroxybutyl-(1→3)-6-O-p-toluenesulfonyl-1,2-dideoxyglucose (4):

Tosyl chloride (15.9 g, 83.2 mmol) is added to an ice-cold solution of 3 (19 g, 69.3 mmol) in pyridine (100 ml). After 18 hours at 0° C., the mixture is concentrated in vacuo, the residue is coevaporated with toluene and taken up in ether and the mixture is washed with water. The organic phase is dried over sodium sulfate and concentrated and the residue is chromatographed (hexane/ethyl acetate 3:1). Yield: 28.5 g (96%).

$^1$H NMR (300 MHz, CDCl$_3$): δ=$^1$H NMR (300 MHz, CDCl$_3$): δ=2.02 (m, 1H, 2-H), 2.4 (s, 3H, CH$_3$), 2.73 (bs, 1H, 4-OH), 3.95 (m, 2H, O—CH$_2$—CH=CH$_2$), 5.22 (m, 2H, O—CH$_2$—CH=CH$_2$), 5.9 (m, 1H, O—CH$_2$—CH=CH$_2$), 7.32, 7.80 (2m, 4H, H$_{tos}$).

Synthesis of 4-allyloxy-1-hydroxybutyl-1→3)-2-azido-1-hydroxyethyl-(1→6)-1,2-dideoxyglucose (5):

Sodium hydride (1.56 9, 65 mmol) is added to a solution of azidoethanol (5 g, 57.5 mmol) in dimethylformamide (100 ml). After 30 minutes, a solution of 4 (4.93 g, 11.5 mmol) is added dropwise. After 18 hours, water (5 ml) is added, the mixture is diluted with ether and the organic phase is washed with water and then concentrated. The residue is purified by chromatography (hexane/ethyl acetate 2:1→1:1). Yield: 3.58 g (91%).

$^1$H NMR (300 MHz, CDCl$_3$): δ=2.02 (m, 1H, 2-H), 2.78 (d, 1H, 4-OH), 3.96 (m, 2H, O—CH$_2$—CH=CH$_2$) 5.22 (m, 2H, O—CH$_2$—CH=CH$_2$), 5.9 (m, 1H, O—CH$_2$—CH=CH$_2$).

Synthesis of 4-allyloxy-1-hydroxybutyl-(1→3)-[(2,3,4-tri-O-benzyl-α-L-fucopyranosyl)-(1→4)]-2-azido-1-hydroxyethyl-(1→6)-1,2-dideoxyglucose (6):

A 0.1M trimethylsilyl trifluoromethanesulfonate solution (0.51 ml) is added to a solution of 5 (1.76 g, 5.13 mmol) in ether (30 ml), and a solution of O-(2,3,4-tri-O-benzyl-L-fucopyranosyl) trichloroacetimidate is then added dropwise in the course of 15 minutes. After a further 15 minutes, the mixture is neutralized with sodium bicarbonate (0.5 g) and filtered and the filtrate is concentrated. Chromatography (methylene chloride/methanol 80:1) gives 6 (3.43 g, 88%).

Synthesis of 1,4-dihydroxybutyl-(1→3)-[(2,3,4-tri-O-benzyl-α-L-fucopyranosyl)-(1→4)]-2-azido-1-hydroxyethyl-(1→6)-1,2-dideoxyglucose (7):

A solution of prehydrogenated bis(methyldiphenylphosphine)cyclooctadieneiridium(I) hexafluorophosphate (52 mg, 0.06 mmol) in THF (5 ml) is added to a solution of 6 (3.43 g, 4.52 mmol) in tetrahydrofuran (34 ml). After 90 minutes, water (2 ml) and iodine (1.076 g) are added and the mixture is stirred for a further 2 hours. It is diluted with methylene chloride and washed with a 20% strength sodium thiosulfate solution and then with water. The residue obtained after concentration is chromatographed (hexane/ethyl acetate 1:1→2:1). Compound 7 (2.21 g, 68%) is obtained.

Synthesis of 4-tosyloxy-1-hydroxybutyl-(1→3)-[(2,3,4-tri-O-benzyl-α-L-fucopyranosyl-(1→4)]-2-azido-1-hydroxyethyl-(1→6)-1,2-dideoxyglucose (8):

Tosyl chloride (212 mg, 1.11 mmol) is added to an ice-cold solution of 7 (618 mg, 0.86 mmol) in pyridine (5 ml). After 24 hours, the mixture is concentrated in vacuo, the residue is coevaporated with toluene and taken up in ether and the mixture is washed with water. The organic phase is dried over sodium sulfate and filtered and the filtrate is concentrated. Chromatography (hexane/ethyl acetate 3:1→2:1) gives compound 8 (533 mg, 71%).

$^1$H NMR (300 MHz, CDCl$_3$): δ=1.09 (d, 3H, 6-H$_{fuc}$), 2.43 (s, 3H, CH$_3$), 5.05 (d, 1H, 1-H).

Synthesis of 4-dimethylmalonyl-1-hydroxybutyl-(1→3)-[(2,3,4-tri-O-benzyl-δ-L-fucopyranosyl)-(1→4)]-2-azido-1-hydroxyethyl-(1→6)-1,2-dideoxyglucose (8):

A mixture of 8 (986 mg, 1.13 mmol), dimethyl malonate (17 ml), potassium carbonate (1.08 g) and dibenzo-18-crown-6 is stirred at 100° C. for 1 hour. It is diluted with ethyl acetate and filtered over silica gel and the residue is concentrated under a high vacuum at 70° C. Chromatography (hexane/ethyl acetate 3:12:1) gives 8 (684 mg, 73%).

$^1$H NMR (300 MHz, CDCl$_3$): δ=1.12 (d, 3H, 6-H$_{fuc}$), 3.72 (2s, 6H, 2CH$_3$), 5.05 (d, 1H, 1-H).

Synthesis of 4-malonyl-1-hydroxybutyl-(1→3)-[α-L-fucopyranosyl-(1→4)]-2-amino-1-hydroxyethyl-(1→6)-1,2-dideoxyglucose (9):

2M sodium hydroxide solution is added successively to a solution of 8 (506 mg, 0.608 mmol) in methanol in an amount just short of precipitation. When hydrolysis is complete, the mixture is neutralized with Amberlite® IR-120 and filtered and the filtrate is concentrated. The residue is taken up in dioxane/water (9:1, 15 ml), palladium-on-charcoal (10%, 400 mg) is added and hydrogenation is carried out in a hydrogen atmosphere for 18 hours. Filtration and chromatography by means of Biogel® P2 give 9 (281 mg, 91%).

$^1$H NMR (300 MHz, D$_2$O): δ=1.06 (d, 3H, 6-H$_{fuc}$), 1.18 (m, 4H, 2 CH$_2$), 1.45 (2m, 3H, 1-H, CH$_2$), 1.60 (m, 2H, CH$_2$), 2.14 (m, 1H, 1-H), 4.26 (q, 1H, 5-H$_{fuc}$), 4.74 (d, 1H,1 H$_{fuc}$).

EXAMPLE 2

Poly-D,L-succinimide-co-α,β-(5-carboxypentyl)-D,L-aspartamide 500 mg of PSI (molecular weight 9 600) are dissolved in 2 ml of DMF, and 1.38 g of 6-aminohexanoic acid, dissolved in 8 ml of formamide, and 1 ml of triethylamine are added.

The mixture is stirred at 45° C. for 13 hours and then precipitated with 1-butanol. After the polymer has been washed with methanol, it is taken up in $H_2O$ and freeze dried.

Yield: 350 mg

Degree of substitution according to NMR: 8% of aminohexanoic acid

EXAMPLE 3

Poly-D,L-succinimide-co-α,β-(5-carboxypentyl)-D,L-aspartamide 1 g of PSI (molecular weight 24 000) is dissolved in 4 ml of DMF, and 2.1 g of 6-aminohexanoic acid, dissolved in 10 ml of formamide, and 25 mg of DMAP are added. The mixture is stirred at room temperature for 3 days and at 45° C. for 9 hours and then precipitated with 1-butanol. After the polymer has been washed with methanol, it is taken up in $H_2O$ and freeze dried.

Yield: 980 mg

Degree of substitution according to NMR: 18% of aminohexanoic acid.

EXAMPLE 4

Poly-D,L-succinimide-co-α,β-(2-carboxyethyl)-D,L-aspartamide 5 g of PSI (molecular weight 9 600) are dissolved in 20 ml of DMF, and 7.5 g of β-alanine, dissolved in 50 ml of formamide, and 100 mg of DMAP are added. The mixture is stirred at room temperature for 3 days and at 45° C. for 9 hours and then precipitated with 1-butanol. After the polymer has been washed with methanol, it is taken up in $H_2O$ and freeze dried.

Yield: 3.9 g

Degree of substitution according to NMR: 14% of β-alanine

EXAMPLE 5

Poly-D,L-succinimide-co-α,β-(2-(2-hydroxymethyl)-carboxyethyl)-D,L-aspartamide 1 g of PSI (molecular weight 9 600) is dissolved in 4 ml of DMF, and 1.5 g of L-serine, dissolved in 8 ml of formamide, and 4 ml of triethylamine are added. The mixture is stirred at room temperature for 3 days and at 45° C. for 9 hours and then precipitated with 1-butanol. After the polymer has been washed with methanol, it is taken up in $H_2O$ and freeze dried.

Yield: 1 g

Degree of substitution according to NMR: 14% of L-serine

EXAMPLE 6

Coupling of the polymer from Example 2 with compound 9 (from Example (1)

100 mg of PCPA from Example 2 are dissolved in 2 ml of $H_2O$, and 20 mg of compound 9 (from Example 1) are added. 4 portions of 20 mg each of 1-ethyl-3-(3-dimethylaminopropyl)-carbodiimide hydrochloride (EDC) are added in the course of 36 hours. After dialysis and freeze drying, the product remains.

Yield: 112mg

Degree of substitution according to NMR: 5% of compound 9

EXAMPLE 7

Coupling of the polymer from Example 3 with compound 9 (from Example 1)

100 mg of PCPA from Example 3 are dissolved in 2 ml of $H_2O$, and 20 mg of compound 9 (from Example 1) are added. 4 portions of 20 mg each of 1-ethyl-3-(3-dimethylaminopropyl)-carbodiimide hydrochloride (EDC) are added in the course of 36 hours. After dialysis and freeze drying, the product remains.

Yield: 90 mg

Degree of substitution according to nmr: 12% of compound 9

We claim:

1. A compound consisting of a polyamino acid linked to at least one moiety of formula II

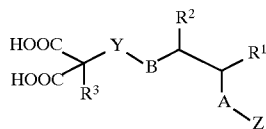

wherein $R^1$ and $R^2$ together form to a six-membered carbocyclic or heterocyclic group having at least one ring substituent selected from the group consisting of $R^4$, $R^5$, and $R^6$, $R^4$, $R^5$, and $R^6$ independently are selected from the group consisting of H, OH, —O—$(CH_2)^q X^4$, $CH_2O(CH_2)_q X^5$, and $HNC(O)CH_3$, $R^3$ is H, $(CH_2)_m X$ or $CH_2O(CH_2)_m X^1$, A and B independently are selected from the group consisting of O, S, NH, HN—CO, OC—NH, O—CO, OC—O, NH—CO—O, —O—CO—NH, S—CO, SC—O, O—CS—S, S—CS—O, NH—CS—S, S—CS—NH, and $CH_2$, Z is a pyranose, a furanose, an open-chain polyalcohol or Y—$X^6$, Y is —O—$(CX^2X^3)_n$, —$(CX^2X^3)_n$, or —$CH_2$—$(CX^2X^3)_m$, X, $X^1$, $X^2$, and $X^3$ independently are selected from the group consisting of H, $NH_2$, COOH, OH, $CH_2OH$, $CH_2NH_2$, $C_1$–$C_{20}$-alkyl, and $C_6$–$C_{10}$-aryl, $X^4$ and $X^5$ independently are —NH— or —O—, $X^6$ is OH or —$C(R^3)$ $(COOH)_2$, m, n, and q independently are 1–20, and wherein said polyamino acid and said moiety of formula I are linked either:

(a) directly through one of the ring substituents $R^4$, $R^5$, or $R^6$; or (b) by a spacer of the formula —$Q^1$—$(CH_2)_p$—$Q^2$—, wherein $Q^1$ is $CH_2$ or —CO—, $Q^2$ is —NH— or —CO—NH—, and p is 1–6.

2. A compound as claimed in claim 1, in which the polyamino acid is polysuccinimide.

3. A compound as claimed in claim 1, in which the polyamino acid is polyaspartamide.

4. A compound as claimed in claim 1, in which the polyamino acid is polyglutamate.

5. A compound as claimed in claim 1, in which the polyamino acid is polylysinefumaramide.

6. A compound as claimed in claim 1, in which the polyamino acid is a copolymer of polysuccinimide and polyaspartamide.

7. A compound as claimed in claim 1, in which the polyamino acid is a copolymer of polyhydroxyethylaspartamide and polyaspartamide.

8. A compound as claimed in claim 1, in which the polyamino acid is a copolymer of polysuccinimide, polyaspartamide and polyhydroxyethylaspartamide.

9. A compound as claimed in claim 1, in which $R^1$ and $R^2$ together form a substituted tetrahydropyran ring, A and B are O, Z is a -fucopyranosyl group and Y is $(CX^2,X^3)_n$, in which
$R^3, X^2$ and $X^3$ are H and n is 5.

10. A compound as claimed in claim 9, in which the substituents of the tetrahydropyran ring $R^4$ and $R^5$ are each H, the substituent $R^6$ in the tetrahydropyran ring between the ring hetero atom O and the ring substituent —A—Z is —CH$_2$O(CH$_2$)$_q$X$^5$ and $X^5$ is —NH—.

11. A compound as claimed in claim 10, in which q is 2.

12. A compound as claimed in claim 9, in which the tetrahydropyran ring is a pyranose.

13. A compound as claimed in claim 12, in which the pyranose is N-acetyl-D-glucosamine.

14. A compound as claimed in claim 1, in which $R^1$ and $R^2$ together are a six-membered carbocyclic radical, A—Z is $$-\overset{H}{\underset{|}{N}}-\overset{O}{\underset{\|}{C}}-(CX^2,X^3)_n-CH_2-X^6,$$

—B—Y— is $$-\overset{H}{\underset{|}{N}}-\overset{O}{\underset{\|}{C}}-(CX^2,X^3)_n-CH_2,$$

$R^3$ and $X^2$ are H,
$X^3$ and $X^6$ are OH and
n is 4.

15. A compound as claimed in claim 14, in which $X^6$ is $$-\overset{COOH}{\underset{H\diagdown COOH}{\underset{|}{C}}}$$

16. A process for the preparation of a compound as claimed in claim 1, which comprises achieving the covalent linkage of the polymer with a compound of the formula III $$\text{HOOC}\underset{R^3}{\overset{Y}{\diagup}}\overset{(D)}{\underset{B}{\diagdown}}\underset{A}{\overset{}{\diagdown}}_Z\!-\!E-(Q^1-(CH_2)_p)_r-Q^3,$$ III in which (D) is —NH—, —O— or —CH$_2$—, E if r=1 is —O—(CH$_2$)$_q$—NH—, —O—(CH$_2$)$_q$—O—, —CH$_2$O(CH$_2$)$_q$—NH— or —CH$_2$O(CH$_2$)$_q$—O— and if r=0 is —O—(CH$_2$)$_q$—, —O—(CH$_2$)$_q$—, —CH$_2$O(CH$_2$)$_q$— or —CH$_2$O(CH$_2$)$_q$—O— and $Q^3$ is —OH, —NH$_2$ or $$\overset{O}{\underset{\|}{-C}}-OH$$

and the other variables have the meanings given in claim 1, by reaction between a reactive and an activated group.

17. A medicament comprising a compound as claimed in claim 1 and a pharmaceutical carrier.

18. A method of preparing a medicament comprising admixing a compound according to claim 1 with a pharmaceutical carrier.

19. A method of treatment or prophylaxis of a selectin-mediated disease, comprising administering to a patient in need thereof a compound according to claim 1.

20. A method according to claim 19, wherein said selectin-mediated disease is selected from the group consisting of bacterial and viral infections, inflammatory processes, and metastasizing tumors.

* * * * *